United States Patent [19]
Natt et al.

[11] Patent Number: 6,107,479
[45] Date of Patent: Aug. 22, 2000

[54] PROCESS FOR THE PREPARATION OF AN OLIGOMERIC COMPOUND

[75] Inventors: François Natt, Aesch; Robert Häner, Fehren, both of Switzerland

[73] Assignee: Novartis AG, Basel, Switzerland

[21] Appl. No.: 09/297,709

[22] PCT Filed: Nov. 5, 1997

[86] PCT No.: PCT/EP97/06123

§ 371 Date: May 6, 1999

§ 102(e) Date: May 6, 1999

[87] PCT Pub. No.: WO98/20018

PCT Pub. Date: May 14, 1998

[30] Foreign Application Priority Data

Nov. 7, 1996 [EP] European Pat. Off. ............. 96117847

[51] Int. Cl.$^7$ .......................... C07H 21/00; C07H 21/02; C07H 21/04
[52] U.S. Cl. .................... 536/25.4; 536/25.3; 536/25.31; 536/25.32; 536/23.1; 435/91.1
[58] Field of Search .................. 536/25.4, 23.1, 536/25.3, 25.31, 25.32; 435/91.1

[56] References Cited

U.S. PATENT DOCUMENTS 5,464,759  11/1995  Coolidge et al. ..................... 435/91.2

FOREIGN PATENT DOCUMENTS 0 294 196 A2  6/1988  European Pat. Off. .

OTHER PUBLICATIONS

Altmann K.–H. et al., Chimia, vol. 50 (4), "Second Generation of Antisense Oligonucleotides: From Nuclease Resistance to Biological Efficacy in Animals," pp. 168–176 (1996).
Beaucage S. and Iyer R., Tetrahedron, vol. 48 (12), "Advances in the Synthesis of Oligonucleotides by the Phosphoramidite Approach," pp. 2223–2311 (1992).
Beaucage S. and Iyer R., Tetrahedron, vol. 49 (10), "The Functionalization of Oligonucleotides Via Phosphorimidite Derivatives," pp. 1925–1963 (1993).
Blackburn G.M. and Guo M.–J., Tetrahedron Letters, vol. 34 (1), "Trifluoromethylphosphinyl Bis–Triazolides in the Synthesis of Trifluoromethylphosphonate Analogues of Nucleotides," pp. 149–152 (1993).
De Mesmaeker A. et al., Acc. Chem. Res., vol. 28, "Antisense Oligonucleotides," pp. 366–374 (1995).
De Mesmaeker A. et al., Current Opinion in Structural Biology, vol. 5, "Backbone modifications in oligonucleotides and peptide nucleic acid systems," pp. 343–355.
Garcia–Echeverria C. and Häner R., Tetrahedron, vol. 52 (11), "A Convenient Method for the Preparation of Oligonucleotide 5'–Phosphates," pp. 3933–3938 (1996).
MacKellar C. et al., Nucleic Acid Research, vol. 20 (13), "Synthesis and physical properties of anti–HIV antisense oligonucleotides bearing terminal lipophilic groups," pp. 3411–3417 (1992).
Natt F. and Häner R., Tetrahedron, vol. 53 (28), "*Lipocap*: a Lipophilic Phosphoramidite–based Capping Reagent," pp. 9629–9636 (1997).
Peiles U. et al., Nucleic Acids Research, vol. 21 (14), "Matrix–assisted laser desorption ionization time–of–flight mass spectrometry: a powerful tool for the mass and sequence analysis of natural and modified oligonucleotides," pp. 3191–3196. (1993).
Roelen H.C.P.F. et al., Tetrahedron Letters, vol. 33 (17), "Synthesis of Alkylphosphon(othio)ate Analogues of DNA," pp. 2357–2360 (1992).
Yu D. et al., Tetrahedron Letters, vol. 35 (46), "Diethoxy N, N–diisopropyl Phosphoramidite as an Improved Capping Reagent in the Synthesis of Oligonucleotides Using Phosphoramidite Chemistry," pp. 8565–8568 (1994).

*Primary Examiner*—George C. Elliott
*Assistant Examiner*—Janet L. Epps
*Attorney, Agent, or Firm*—Myra H. McCormack

[57] ABSTRACT

The present invention relates to a process for the preparation of an oligomeric compound, comprising introduction of a lipophilic capping group to an unreacted reactive group, suitable for chain elongation, of a not elongated oligomeric compound intended to be elongated in a preceeding chain-elongation step, by reacting a lipophilic capping compound with said unreacted reactive group, which lipophilic capping group is not removable under the applied conditions of the synthesis and work-up of the oligomeric compound; and which not elongated oligomeric compound capped with said lipophilic capping group can be separated from said oligomeric compound on a hydrophobic stationary phase.

17 Claims, No Drawings

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(20)
<223> OTHER INFORMATION: phosphorothioate backbone

<400> SEQUENCE: 1
tcccgcctgt gacatgcatt                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(6)
<223> OTHER INFORMATION: 2'-methoxyethoxy substitutent
<220> FEATURE:
<221> NAME/KEY: misc_feature
<222> LOCATION: (6)..(15)
<223> OTHER INFORMATION: phosphorothioate backbone
<220> FEATURE:
<221> NAME/KEY: misc_feature
<222> LOCATION: (15)..(20)
<223> OTHER INFORMATION: 2'-methoxyethoxy substituent

<400> SEQUENCE: 2
tcccgcctgt gacatgcatt                                              20

-continued

```
<210> SEQ ID NO 3
<211> LENGTH: 9
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(9)
<223> OTHER INFORMATION: phosphorothioate backbone

<400> SEQUENCE: 3 acatgcatt                                                                9

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(19)
<223> OTHER INFORMATION: phosphorothioate backbone

<400> SEQUENCE: 4
cccgcctgtg acatgcatt                                                    19
```

PROCESS FOR THE PREPARATION OF AN OLIGOMERIC COMPOUND

The present application is directed to a process for the preparation or purification of an oligomeric compound.

Oligomeric compounds, in particular biopolymers such as oligonucleotides, have attracted great attention because of their potential therapeutic applicability. For example, the use of oligonucleotides in antisense-technology-based therapy is subject of intensive research. Accordingly, there is a need for providing processes for the preparation or purification of oiigomeric compounds.

Oligomeric compounds, for example oligonucleotides, which structure comprises a chain of building blocks, are frequently synthesized by consecutive reaction cycles, whereby each reaction cycle comprises a step of chain elongation by reacting the growing chain of the oligomeric compound with the next chain building block. However, such a chain elongation step frequently does not go to completion so that not elongated oligomeric compounds result, which do not extend to the intended full length. In order to prevent undesired further chain elongation of such unreacted, not extended oligomeric compounds in subsequent reaction cycles, a capping step is used in each cycle to inactivate said unreacted reactive group. Furthermore, not elongated oligomeric compounds have to be separated from the final, full length oligomeric compound in the course of the preparation process.

For example, a common approach for the synthesis of oligonucleotides is the solid phase method using phosphoramidite chemistry (S. L. Beaucage and R. P. lyer, Tetrahedron 48 (1992), pp. 2223–2311), using for example acetic anhydride as capping reagent. An oligonucleotide synthesized according to this procedure usually has to be purified from undesired failure sequences. For the typical purification procedure the final terminal protecting trityl-group is not removed ("trityl-on") during oligonucleotide synthesis. Rather, the trityl-bearing full length oligonucleotide is separated from failure sequences by reverse phase HPLC. However, this method displays two main disadvantages: a) it requires a post-purification chemical treatment (removal of the trityl-group with aqueous acetic acid) and b) the relative instability of a trityl-group, like 4,4'-dimethoxytrityl (DMT), may lead to the loss of some full-length oligonucleotides due to unwanted detritylation during the purification procedure.

It is an object of the present invention to provide a process for the preparation of an oligomeric compound.

It is a further object of the present invention to provide a process for the purification of an oligomeric compound.

According to an aspect of the present invention, a process is provided for the preparation of an oligomeric compound, comprising introduction of a lipophilic capping group to an unreacted reactive group, suitable for chain elongation, of a not elongated oligomeric compound intended to be elongated in a preceeding chain-elongation step, by reacting a lipophilic capping compound with said unreacted reactive group, which lipophilic capping group is not removable under the applied conditions of the synthesis and work-up of the oligomeric compound; and which not elongated oligomeric compound capped with said lipophilic capping group can be separated from said oligomeric compound on a hydrophobic stationary phase. In this context, the term "not elongated oligomeric compound" designates an oligomeric compound not extented to its desired full length.

In a further embodiment, the process of preparation according to the present invention further comprises, after completion of the chain elongation of the oligomeric compound, full deprotection of the oligomeric compound, where a protected oligomeric compound is present. Full deprotection comprises deprotecting the terminal reactive group of the chain as well as any other protected group present in the oligomeric compound to be synthesized.

In a further embodiment, the process of preparation according to the present invention further comprises the separation of the fully deprotected oligomeric compound from the thus capped, not elongated oligomeric compound on a hydrophobic stationary phase.

Accordingly, another aspect of the present invention relates to a process for purification of an oligomeric compound, comprising the separation of a not elongated oligomeric compound capped with a lipophilic capping group from said oligomeric compound, which capped, not elongated oligomeric compound is obtainable by reaction of a lipophilic capping compound with an unreacted reactive group of a not elongated oligomeric compound intended to be elongated in a preceeding chain-elongation step, and which lipophilic capping group is not removable under the applied conditions of the synthesis and work-up of the oligomeric compound, on a hydrophobic stationary phase.

In a further embodiment thereof, the process for purification further comprises, before the step of separation, full deprotection of the oligomeric compound, where a protected oligomeric compound is present, as stated above.

In the process for purification, preferred embodiments, for example with regard to the oligomeric compound, the unreacted reactive group or the lipophilic capping compound are those which are preferred in the context of the process of preparation according to the present invention.

In the process of preparation or purification according to the present invention, an oligomeric compound may in particular be a compound composed of single building blocks. Preferably, such an oligomeric compound may be suitable for synthesis via consecutive reaction cycles, each cycle comprising a chain-elongation step.

In the process of preparation or purification of an oligomeric compound according to the present invention, a typical preparation or purification scheme may comprise the following steps:

There may be provided a first building block being part of a growing chain of the oligomeric compound to be prepared, which oligomeric compound may be bound onto a solid support, said first building block having a reactive site intended to be utilized in chain elongation, while other reactive sites, if present in the building block, being suitably protected. For the step of chain elongation the next building block, which is suitably protected at the reactive site intended to be used for further chain elongation in the reaction cycle, which further is suitably protected on any further reactive site, if present, and which further is suitably activated at the site intended to form the linkage to the first building block, is reacted with the first building block. In the following step of capping of not elongated oligomeric compounds, i.e. oligomeric compounds which have not been elongated in the preceeding chain elongation step of the synthesis procedure of an oligomeric compound, for example due to inefficient reaction, which not elongated oligomeric compounds still bear an unreacted reactive group suitable for chain elongation, a lipophilic capping group is introduced to said unreacted reactive group by reacting a lipophilic capping compound with said unreacted reactive group, which lipophilic capping group is not removable, in contrast to protective groups used in the process, under the applied conditions of the synthesis and work-up of the oligomeric compound; and which not elongated oligomeric compound capped with said lipophilic capping group can be separated from the desired full-length oligomeric compound on a hydrophobic stationary phase. Examples and preferences for such a lipophilic capping compound are given hereinbelow. Subsequent to the step of capping, if necessary or desired the lipophilic capping group thus formed on the not elongated oligomeric compound and/or the linkage formed between the first and the next building block may be stabilized, e.g. by oxidation. In the next step the protective group present on the reactive group intended for further chain elongation of the chain-elongated oligomeric compound is cleaved off, and the cycle is repeated until an oligomeric compound having the desired length is obtained. After completion of the chain elongation of the oligomeric compound, full deprotection of the oligomeric compound may be performed, where a protected oligomeric compound is present. Finally, the oligomeric compound to be prepared is purified by separating said oligomeric compound from the not elongated oligomeric compound capped with a lipophilic capping group, obtainable as described above, on a hydrophobic stationary phase.

In principle, the process of preparation or the process of purification according to the present invention can be applied on various oligomeric compounds which may be composed of a chain of building blocks. For example, an oligomeric compound is selected from the group consisting of an oligonucleotide, an oligosaccharide or a glycopeptide. If the oligomeric compound is a glycopeptide, the chain elongation step according to the process of preparation of the present invention is directed to the glycosidic moiety. Particularly preferred is a process of preparation or a process of purification according to the present invention wherein said oligomeric compound is an oligonucleotide.

For example, if said oligomeric compound is an oligonucleotide, for example consisting of nucleoside building blocks, it may be synthesized using common phosphoramidite chemistry. Accordingly, in a typical reaction cycle the growing oligonucleotide chain can be bound for example to a controlled pore glass (CPG) or polystyrene support. The reactive site intended to serve for chain elongation, for example a 5'- terminal OH-group, may be protected by a protecting group, for example 4,4'-dimethoxytrityl (DMT). Chain elongation can be performed by coupling of a 5'-trityl-type-protected, 3'-phosphoramidite nucleoside building block to the deprotected, free 5'-OH-group of the growing oligonucleotide chain. In the following capping step a lipophilic capping group can be introduced to an unreacted reactive group, suitable for chain elongation, of a not elongated oligomeric compound (so-called failure sequence), which had been intended to be elongated in the preceeding chain-elongation step but failed to do so, by reacting a lipophilic capping compound with said unreacted reactive group. Examples and preferences for suitable lipophilic capping compounds are given hereinbelow. If necessary or desired, the thus introduced capping group, as well as the internucleosidic linkage having been formed in the chain elongation step, can be stabilized, for example by oxidation or by sulfurisation. In the next step the protected reactive group intended for further chain elongation of the growing oligonucleotide chain is deprotected. For example, a 5'-trityl-like protecting group may be cleaved off by treatment with aqueous acetic acid. This reaction cycle may be repeated as often as required for completion of the oligonucleotide assembly. The resulting oligonucleotide preferably may be of the "trityl-off"-type, i.e., it does not bear any more the protecting group, for example the trityl-type group as mentioned above, at the reactive site. Oligonucleotide cleavage from the support and removal of any base labile protecting groups, if present, may be performed by ammonia treatment. For separation of the desired, full-length oligonucleotide from the thus capped not elongated oligonucleotide the mixture comprising the oligonucleotide and the not elongated, capped oligonucleotide is applied on a suitable hydrophobic stationary phase where separation is performed for example by reverse phase HPLC on a suitable support.

The term "oligonucleotide" refers to an oligomeric compound composed of a chain of nucleoside building blocks which are connected via internucloside linkages. Such nucleoside building blocks can be naturally occuring building blocks, like deoxyribonucleosides or ribonucleosides, or they can be modified or synthetic nucleoside or nucleoside analogue building blocks, which still may retain their ability for base-pairing with a complementary nucleic acid strand. In this sense, base pairing can for example be of the Watson-Crick type or of the Hoogsteen-type. Various examples for modified or synthetic nucleoside building blocks are known in the art (see, for example, A. De Mesmaeker et al., Acc. Chem. Res. 28 (1995), pp.366–374). For example, if the modified or synthetic nucleoside is composed of a deoxyribose unit, there may be present a 2'-modification, like for example a 2'-methoxyethoxy substituent. On the other hand, the internucleoside linkage can be a naturally occuring inernucleoside linkage, like a phosphodiester linkage, or it can be a modified or synthetic internucleosidic linkage. Various internucleosidic linkages are known in the art (see, for example, A. De Mesmaeker et al., Current Opinion in Structural Biology 5 (1995), pp. 343–355). For example, such an internucleosidic linkage can be of the phosphorothioate or amide type.

In order to be suitable for base pairing as stated above a nucleoside building block may bear a nucleic base. Suitable nucleic bases are known in the art and can be naturally occuring bases or modifed bases, for example adenine, guanine, cytosine, thymine, uracil, xanthine, hypoxanthine, 2-aminoadenine, 6-thioguanine, 5-methylcytosine, 5-propynyluracil, 5-fluorouracil or 5-propynylcytosine.

An oligonucleotide intented to be prepared or purified in a process according to the present invention can be composed of identical nucleosidic building blocks and/or identical internucleosidic linkages, or it can be composed of different nucleoside building blocks and/or different internucleoside linkages, the different blocks or linkages for example being arranged in an alternating way. Another example is a chimeric oligonucleotide being composed of two, three or more different regions, each region being composed of the same type of nucleoside building blocks and/or internucleoside linkages which are different to those in adjacent regions. Such oligonucleotides may be useful for example in antisense-technology (see, for example, K. -H. Altmann et al., Chimia 50 (1996), pp. 168–176).

An oligonucleotide within the meaning according to the present invention may be of variable length, depending for example on its intended use. For example, an oligonucleotide prepared or purified according to the process of the present invention may be used as a probe or a primer in molecular biology applications like cloning, or in diagnosis, said oligonucleotide optionally being suitably labelled. Another possibility is the use of such an oligonucleotide in antisense-technology-based or triplex-technology-based therapy. Hence, such an oligonucleotide may be composed for example of 2 to 200 or even more building blocks, or 7 to 100, or 7 to 25 building blocks.

In a process of preparation or purification according to the present invention, inclusive the respective preferences, said unreacted reactive group is a group suitable for chain elongation, in particular of a not elongated oligomeric compound having been intended to be elongated in a preceeding chain-elongation step. In a preferred embodiment of the process of preparation or process of purification according to the present invention, inclusive the respective preferences, said unreacted reactive group is a hydroxy group. For example, if said oligomeric compound is a not elongated oligosaccharide or a glycopeptide being not elongated at the glycosidic moiety, the hydroxy group may be the hydroxy group of the sugar ring having been intended for further chain elongation. If said oligomeric compound is an oligonucleotide, for example the hydroxy group may be the 3'-terminal or, preferably, the 5'-terminal hydroxy group of the ribose unit of the nucleoside building block, depending for example on the particular method of synthesis carried out.

The lipophilic capping compound according to the process of preparation or purification is a compound which forms upon reaction with said unreacted reactive group, optionally upon a further stabilizing reaction, like an oxidation, a lipophilic capping group which is not removable under the applied conditions of the synthesis and work-up of the oligomeric compound and which further allows the not elongated oligomeric compound capped with said lipophilic capping group to be separated from the full-length oligomeric compound on a hydrophobic stationary phase, in particular using chromatographic techniques, for example reverse phase HPLC. A skilled person will be readily aware of hydrophobic stationary phase materials, which are also known as reverse-phase materials or hydrophobic interaction materials, suitable for the process of preparation or purification according to the present invention. Preferentially, the surface of the core material, which may be, for example, silica or polystyrene, is functionalized, for example, with a $C_2$–$C_{18}$-alkyl chain or with a phenyl group, $C_{18}$-alkyl being preferred.

In a preferred embodiment of the process of preparation or of purification according to the present invention, in particular, if the unreacted reactive group is a hydroxy group, said lipophilic capping compound can be a compound selected from the group consisting of formula (I), (II), (III) and (IV)

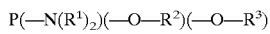  (I),

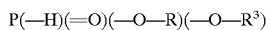  (II),

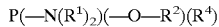  (III),

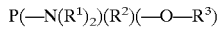  (IV), wherein
$R^1$ is alkyl, or $R^1$ together with the adjacent nitrogen atom forms a N-morpholino or N-pyrrolidino ring;
$R^2$ is a lipophilic substituent;
$R^3$ is a base-labile protecting group or a lipophilic substituent;
$R^4$ is a lipophilic substituent;
and wherein the lipophilic substituent forms a linkage to the adjacent respective oxygen or phosphorus atom which is stable under the applied conditions of synthesis and work-up of the oligomeric compound. In a preferred embodiment thereof, said lipophilic substituent is not bound via a fully substituted C-atom of an alkyl group to the respective adjacent oxygen atom or phosphorus atom. This preferred embodiment is primarily due to stability requirements imposed by reaction conditions which may be applied during synthesis and work-up of the oligomeric compound.

For further stabilisation, subsequent to introducing the lipophilic capping group by using a lipophilic capping compound of formula (I), (II), (III) or (IV), the valence of the phosphorus atom of said lipophilic capping group is increased to a valence of 5, for example by oxidation or sulfurisation, this procedure being known in the art.

A lipophilic substituent possesses a lipophilicity or hydrophobicity sufficient in order for the capped not elongated oligomeric compounds to be separable from the full-length oligomeric compound on a hydrophobic stationary phase according to the process of the present invention.

Preferably, the lipophilic substituent shows sufficient lipophilicity if it, for example, comprises at least one aryl or aralkyl group, wherein aryl or aryl of aralkyl is an aromatic ring comprising at least 6 C-atoms; or if said substituent comprises at least one linear alkyl backbone or linear alkyl chain composed of at least 4, preferably at least 5, more preferably at least 6, adjacent C-atoms. Said linear backbone or chain can be embedded in a larger structure, like a branched alkyl chain.

Base-labile protecting groups are known in the art (see, for example, S. Agrawal, "Protocols for Oligonucleotides and Analogues", J. M. Walker (ed.); Humana Press; Totowa, N.J., (1993); or S. Beaucage et al., see above). For example, such a base-labile protecting group is selected from the group consisting of β-cyanoethyl, β-cyano-α-methylethyl, β-cyano-α,α-dimethylethyl, trichloroethyl, allyl, trifluoroethyl, 4-nitrobenzoylethyl, 4-pyridylethyl, 4-chlorobenzyl, phenyl, 4-nitrophenyl and pentachlorophenyl; β-cyanoethyl being preferred.

The substituent —N($R^1$)$_2$ in formula (I), (III) or (IV) for example is N-pyrrolidino, N-morphoiino or an alkyl group—bearing substituent suitable for phosphoramidite chemistry, for example suitable to be activated by tetrazole, as described for example in S. L. Beaucage and R. P. Iyer, Tetrahedron 48 (1992), pp. 2223–2311. In this context a suitable alkyl group for example is isopropyl or ethyl; isopropyl being preferred.

Preferably, the lipophilic compound according to the process of preparation or purification of the present invention, in particular if said unprotected reactive group is a hydroxyl group, may be a compound of formula (I)

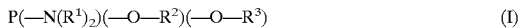  (I)

wherein $R^1$, $R^2$ and $R^3$ are as defined above, inclusive the respective preferences as stated herein.

In a preferred aspect of the process of preparation or purification according to the present invention, inclusive the respective preferred embodiments, said lipophilic substituent of the formula (I), (II), (III) or (IV) may be of formula (V)

  (V)

wherein
m is an integer from 1 to 35, preferably from 1 to 18;
n is 0 or 1;
$R^5$ and $R^6$ independently are H, branched or unbranched alkyl, unsubstituted or ring substituted aryl, or unsubstituted or ring substituted aralkyl, wherein the substituent of said substituted aryl or aralkyl is selected from the group consisting of branched or unbranched alkyl, aryl and aralkyl;

X is O, S or $NR^8$;

$R^7$ is H or branched or unbranched alkyl; and $R^8$ is branched or unbranched alkyl, aralkyl or aryl;

wherein aryl or aryl of aralkyl is an aromatic ring composed of at least 6 C-atoms; and wherein the substituent of formula (V) comprises at least one aryl or aralkyl substituent, or it comprises at least one linear alkyl backbone composed of at least 4, preferably of at least 5, more preferred of at least 6, adjacent C-atoms.

As stated above, the structural requirements for the substituent of formula (V) primarily result from the necessary lipophilicity or hydrophobicity the capped not elongated oligomeric compounds should possess in order to be separatable from the full-length oligomeric compound on a hydrophobic stationary phase according to the process of the present invention. A skilled person will be readily aware of suitable alkyl, aryl or aralkyl residues.

For example, if in the substituent of formula (V) no aryl or aralkyl group is present, alkyl may be selected from the group consisting of n-butyl, n-pentyl, n-hexyl, n-octyl, n-nonyl, n-decyl and larger members of the n-alkyl series, like n-$C_{11}$-, n-$C_{12}$-, n-$C_{13}$-, n-$C_{14}$-, n-$C_{15}$-, n-$C_{16}$-, n-$C_{17}$- or n-$C_{18}$-alkyl, or even higher members of the n-alkyl series up to n-$C_{35}$-alkyl, or yet even higher members of the n-alkyl series. If in this context alkyl is an alkyl group composed of at least 7 $CH_2$-groups, any isomeric form of said alkyl groups may be used as substituent in formula (V) according to the present invention, however, taking into account the structural requirements as stated above. If the substituent of formula (V) comprises at least one aryl or aralkyl group, the remaining alkyl group, if present, may be of any type, like, for example, lower alkyl, like methyl, ethyl, iso- or n-propyl, iso-, tert- or n-butyl, or larger residues. The linear alkyl backbone as stated above may be embedded in at least one of the substituents $R^5$, $R^6$, $R^7$, or $R^8$, or the substituent of formula (V as a whole may comprise such a backbone. Preferably, said linear alkyl backbone may be included in at least one of the substituents $R^5$, $R^6$ or $R^7$, in which case $R^8$ preferably is alkyl, more preferred lower alkyl, like methyl, ethyl, iso- or n-propyl, iso-, tert- or n-butyl, in particular methyl or ethyl. More preferably, said linear alkyl backbone may be included in at least one of the substituents $R^5$, or $R^6$, in which case $R^7$, for example, may be H or lower alkyl, like methyl, ethyl, iso- or n-propyl, iso-, tert- or n-butyl; methyl or ethyl being preferred.

Examples for a preferred aryl group are phenyl or a larger aromatic ring system, like for example anthracyl. Examples for a preferred aralkyl group are benzyl, diphenylmethyl or larger residues. Substituents for aryl or aralkyl may be, for example, aryl, as defined above, or lower alkyl, like methyl, ethyl, iso- or n-propyl, iso-, tert- or n-butyl.

In a preferred embodiment of formula (V) n is 0, i.e. no substituent X is present. In this case, the preferences for the substituents $R^5$, $R^6$ or $R^7$ may be as stated above.

In a further preferred embodiment of the process of purification or preparation according to the present invention, the lipophilic substituent is a structure of formula (V) wherein $R^5$ and $R^6$ each are H; $R^7$ is methyl; n is 0; and m is an integer from 3 to 35, preferably from 4 to 35, more preferably from 4 to 18, most preferably m is 7; wherein at least one linear alkyl backbone composed of at least 4, preferably at least 5, more preferably of at least 6, adjacent C-atoms is present in the structure.

A person skilled in the art will readily be aware that particular preferred substituents of formula (V) are those showing a reasonable compromise between lipophilicity, synthesis efficacy and price.

In another preferred embodiment of the procees of preparation or purification according to the present invention, including the respective preferences as stated herein, said lipophilic compound is a compound of formula (I)

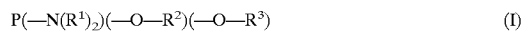

(I)

wherein $R^1$ is isopropyl, $R^2$ is —$(CH_2)_7$—$CH_3$ and $R^3$ is β-cyanoethyl.

Processes for preparing lipophilic compounds of formula (I), (II), (Ill) or (IV) are known in the art or may be readily available for those of skill (see, for example, S. Agrawal, "Protocols for Oligonucleotides and Analogues", J. M. Walker (ed.); Humana Press; Totowa, N.J., (1993)).

For example, a lipophilic compound of formula (I) is obtainable by reacting the phosphitylating reagent of formula (VI)

(VI)

wherein X is halogen, for example Cl, or $N(R^1)_2$, with a compound of formula (VII)

(VII)

wherein $R^1$, $R^2$ and $R^3$ are as defined above, inclusive the respective preferences as stated herein, according to S. Agrawal, see above, pp. 39–44.

A lipophilic compound of formula (II) is obtainable by reacting tris-triazole phosphite with a compound of formula (VII) (see above) or formula (VIII)

(VIII)

wherein $R^3$ is as defined above, inclusive the respective preferences as stated herein, according to S. Agrawal, ibid., pp. 66–68.

A lipophilic compound of formula (III) is obtainable by reacting a compound of formula (IX)

(IX), with a compound of formula (VII), $R^2$—OH, as defined above, according to G. M. Blackburne and M. J. Guo, Tetrahedron Letters 34, pp. 149–152, which compound (IX) is accessible according to H. C. P. F. Roelen et al., Tetrahedron Letters 33 (1992), pp. 2357–2360, by reacting a compound of formula (X)

(X)

wherein X is halogen, like, for example, Cl, with a compound of formula (XIa) or (XIb)

(XIa)

(XIb)

wherein $R^1$, $R^2$ and $R^4$ are as described above, inclusive the respective preferences as stated herein. Compounds of formula (XIa) or (XIb) are readily available according to methods known in the art.

A lipophilic compound of formula (IV) is obtainable by reacting a compound of formula (XII)

(XII)

with a compound of formula (VIII), $R^3$—OH, as defined above, according to G. M. Blackburne and M. J. Guo, Tetrahedron Letters 34, pp. 149–152, which compound (XII) is accessible according to H. C. P. F. Roelen et al., Tetrahedron letters 33 (1992), pp. 2357–2360, by reacting a compound of formula (X)

$$P(-N(R^1)_2)(-X) \quad (X),$$

wherein X is halogen, like, for example, Cl, with a compound of formula (XIIIa) or (XIIIb)

$$R^2-Li, \quad (XIIIa)$$

$$R^2-Mg-Br; \quad (XIIIb)$$

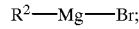

wherein $R^1$, $R^2$ and $R^3$ are as described above, inclusive the respective preferences as stated herein. Compounds of formula (XIIIa) or (XIIIb) are readily available according to methods known in the art.

A further aspect of the present invention relates to the use of a lipophilic compound as reagent for introduction of a lipophilic capping group to an unreacted reactive group, suitable for chain elongation, of a not elongated oligomeric compound intended to be elongated in a preceeding chain-elongation step of the synthesis of an oligomeric compound, which lipophilic capping group is not removable under the applied conditions of the synthesis and work-up of the oligomeric compound, and which not elongated oligomeric compound capped with said lipophilic capping group can be separated from said oligomeric compound on a hydrophobic stationary phase.

Prefered embodiments of the use according to the present invention, in particular with regard to said oligomeric compound, said lipophilic capping compound, said unracted reactive group or said hydrophobic stationary phase, are those which are exemplified or preferred in the context of the process of preparation or purification according to the present invention.

The following examples are shown for illustrative purposes only, and are not intended to limit the scope of this invention.

EXAMPLES

A. Materials

Anhydrous solvents are purchased from Fluka. All reagents are freshly dried. Reagents for oligonucleotide synthesis are purchased from Cruachem. O-β-Cyanoethyl-N,N,N',N'-tetraisopropyl phosphordiamidite is purchased from Aldrich. Column chromatography: silica gel 60 (70–230 mesh, Merck). TLC: Silica gel plates ('Kieselgel' 60 $F_{254}$; Merck); visualization is achieved by treatment with a staining solution (5% phospho-molybdic acid in ethanol) followed by heating. NMR spectra are recorded on a Bruker Avance dpx 400 (400 MHz); chemical shifts d in ppm versus $H_3PO_4$($^{31}$P; external standard).

B. Preparation of Oligonucleotides

1. Synthesis of O-β-cyanoethyl-O-octyl-N,N-diisopropyl Phosphoramidite (1):

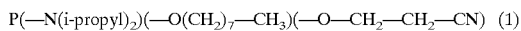

$$P(-N(i\text{-propyl})_2)(-O(CH_2)_7-CH_3)(-O-CH_2-CH_2-CN) \quad (1)$$

O-β-Cyanoethyl-N,N,N',N'-tetraisopropyl phosphordiamidite (76.8 ml) is added to a suspension of diisopropyl ammonium tetrazolide (40.0 g) in 600 ml of dry $CH_2Cl_2$ under an argon atmosphere. n-Octanol (30.4 ml) is dissolved in 100 ml of dry $CH_2Cl_2$ and added dropwise over a period of 20 min. The suspension is stirred 20 h at room temperature. The suspension is washed with $NaHCO_3$ (sat.). The organic layer is collected and washed with $NaHCO_3$ (sat.), dried over sodium sulfate, filtered and evaporated. The residue (63 g), obtained as an oil, is purified by flash column chromatography using diethyl-ether/hexane (1/10) containing 0.5% N-methylmorpholine. Compound (1) is obtained as a colourless oil (yield: 57.12g (90%)). (31P NMR ($CDCl_3$): d 146.269).

2. Synthesis of Oligonucleotides Applying Acetic Anhydride Capping (Standard Procedure, "Trityl-on"):

Oligonucleotides are synthesized on an Applied Biosystems 394B DNA synthesizer using standard chemical protocols based on the O-β-cyanoethyl-phosphoramidite chemistry except for the 2'-methoxyethoxy modified building blocks, for which amidines are used as protecting groups which require 10% ammoinium acetate in the standard ammonia solution used for DNA deprotection. In any case, the 5'-terminal protection group is 4,4'-dimethoxytrityl group (DMT). To prapare a n-mer, the synthesis is stopped after n-1 cycles before the detritylation step. Analytical HPLC runs are carried out with Shandon $RPC_{18}$ ODS Hypersil column (5 mm, 125 mm×4.6 mm) on a Beckman Gold liquid chromatography system. Semi-preparative HPLC runs are carried out with Merck Lichrospher WP 300 RP-18 (LichroCART 10 mm, 250 mm×10 mm) on a Merck-Hitachi liquid chromatography system formed by a L-3000 Photo Diode Array Detector, a L-6200A Intelligent-Pump system, and a D-2500 Chromato-Integrator. Mass spectra are run on an LDI 1700 instrument (Linear Scientific Inc.). Capillary gel electrophoresis (CGE) is performed on a Beckman P/ACE 5010.

3. Synthesis of Oligonucleotides Applying Capping of the Not Elongated Oligonucleotides According to the Present Invention ("Lipocap Capping"):

Oligonucleotides compounds are synthesized using standard chemicals and protocols (see above) in exception of the capping solutions which were set up in the following way: The machine is equipped with a 0.15 M solution of the phosphoramidite (1) (capping solution A), prepared as described above, and with a 0.45 M solution of tetrazole in MeCN (capping solution B). The capping step, i.e. the step of introducing the capping group in the rpcess according to the present invention, is performed by simultaneous delivery of both capping solutions A and B, after the coupling step and before the oxidation or sulfurisation step, to the column.To prepare a n-mer, the synthesis is stopped after n-1 cycles after the step of detrytilation of the 5'-terminal hydroxy group.

Table 1 summarizes essential steps of oligonucleotide synthesis applying the lipocap capping strategy:

TABLE 1

Procedure for the Synthesis of oligonucleotides using phosphoramidite compound (1) as capping reagent

| Step | Reagent/Solvent | Function | Time in sec. per cycle (repeat) |
|---|---|---|---|
| 1 | MeCN | Wash | 20 (2×) |
| 2 | 3% $CCl_3COOH/CH_2Cl_2$ | Detritylation | 40 (3×) |
| 3 | MeCN | Wash | 20 (3×) |
| 4 | Phosphoramidite/tetrazole/MeCN | Coupling | 65 (2×) + 125[a] |
| 5 | MeCN | Wash | 20 (2×) |
| 6 | Lipocap/tetrazole/MeCN[b] | Capping | 70 (3×)[c] |

TABLE 1-continued

Procedure for the Synthesis of oligonucleotides using phosphoramidite compound (1) as capping reagent

| Step | Reagent/Solvent | Function | Time in sec. per cycle (repeat) |
|---|---|---|---|
| 7 | MeCN | Wash | 20 (2×) |
| 8 | Stec's reagent or 0.5M tBuOOH in DCM | Sulfurization or Oxidation | 70 (3×)[c] |
| 9 | MeCN | Wash | 20 (2×) |

[a] delivery = 5 sec. and reaction time = 60 for unmodified phosphoramidites, or 300 sec. for 2'-methoxyethoxy building blocks;
[b] capping solution A: Lipocap (0.15M in MeCN); capping solution B: tetrazole (0.45M in MeCN);
[c] delivery = 10 sec. and reaction time = 60 sec.

4. Deprotection:

All the oligonucleotides are cleaved from the support and deprotected by overnight treatment of the support with concentrated aqueous ammonia at 55° C. (0.5–1 ml for 50 mg of support). The supernatant is collected, the support washed once with nanopure water and the reassembled solutions are lyophilized.

5. Purification:

HPLC runs are performed on Shandon RPC18 ODS Hypersil columns (analytical: 5 mm, 4.6×125 mm) at 1 ml/min or on Merck Lichrospher WP 300 RP-1 8 cartridges (LichroCART 10 mm, 250 mm×10 mm) at 6 ml/min, by using the following mobile phases: Buffer A (50 mM TEM) and Buffer B (MeCN/50 mM TEM, 7:3, v/v), both pH=7.0. Oligonucleotides prepared by applying the trityl-on/acetic anhydride capping—strategy are eluted using the following program: 15% B to 55% B over 40 min; 55% B to 100% B over 1 min and 100% B for 10 min. Oligonucleotides synthesized using the trityl-off/lipocap capping—strategy are eluted using the following program: 5% B to 35 % B over 60 min; 35% B to 100% B over 1 min and 100% B for 10 min.

6. Removal of the Trityl-protectina Group After HPLC Durification:

An oligonucleotide which is prepared according to the trityl-off method applying the lipocap capping procedure according to the present invention as outlined above is ready for further use after the HPLC purification step. In contrast, in order to be ready for further use an oligonucleotide prepared according to the classical trityl-on method applying acetic anhydrid capping as outlined above, is further treated with aqueous acetic acid (80% in water, v/v) according to standard procedure and protocol (see, for example, S. Agrawal, above) for removal of the trityl group.

7. Comparison of Standard Procedure vs. Lipocap Capping Strategy in Oligonucleotide Synthesis:

The following oligonucleotides are synthesized according to the standard procedure (see B.1 above) or the lipocap capping procedure (see B.2 above) and analysed in "head to head" comparison. All syntheses are performed on the 10 μmole scale in "head to head" comparisons. The two oligonucleotides are a phosphorothioate antisense oligodeoxynucleotide (O1) targeting c-raf mRNA, and a mixed (chimeric) phosphodiester/phosphorothioate oligonucleotide (of the same sequence containing deoxynucleotides and 2'-methoxyethoxy modified building blocks (O2). Both oligonucleotides are of current interest as inhibitors of the proliferation of certain tumor cells (K.-H. Altmann et al., Chimia 50 (1996), pp. 168–176).

Oligonucleotide* O1 (SEQ.ID.NO.1): TsCsCsCsGsCsCsTsGsTsGsAsCsAsTsGsCsAsTsT

Oligonucleotide*** O2 (SEQ.ID.NO.2): TCCCGCsCsTsGsTsGsAsCsAsTGCATT

*: "s": phosphorothioate internucleoside linkage;
**: underlined nucleosides N are of the 2'-methoxyethoxy-type:

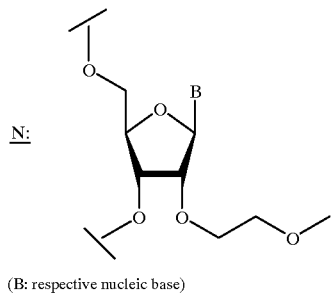

(B: respective nucleic base)

After ammonia deprotection the oligonucleotides are purified by RP-HPLC. Trityl-on fractions are deprotected by treatment with aqueous acetic acid (80% in water, v/v) according to the procedure as outlined above. Table 2 summarizes the yields before and after purification obtained for oligonucleotides (O1) and (O2), prepared either using conventional acetylation capping in combination with trityl-on RP-HPLC purification (entries 1 and 2) or, alternatively, using phosphoramidite compound (1) (see above) as capping reagent in combination with trityl-off RP-HPLC purification (entries 3 and 4). The purity of all materials obtained is controlled by CGE analysis. As can be seen, the lipocap capping strategy affords both oligonucleotides in a significantly higher overall yield (52 and 50%, respectively), as compared to the classical procedure (47 and 42%, respectively).

TABLE 2

Data of the Head-to-Head Comparison at 10 mmole Scale.

| Entry | Method | Compound | Crude Material ($OD_{260}$) | Purified Material ($OD_{260}$) | (%) |
|---|---|---|---|---|---|
| 1 | Acetic anhydride capping | 01 | 1366 | 642 | 47 |
| 2 | and trityl-on purification | 02 | 1357 | 556 | 41 |
| 3 | Lipocap capping | 01 | 1334 | 696 | 52 |
| 4 | and trityl-off purification | 02 | 1250 | 625 | 50 |

8. Analysis of Oligonucleotide Synthesis Performed by Application of the Lipocap Capping Strategy:

The following three experiments are performed: a) the trityl-off lipocap capping—strategy synthesis (see above) of the oligodeoxyribonucleotide phosphorothioate 20-mer O1 (see above) using the phosphoramidite compound (1) (see above) as the capping reagent; b) and c) the same experiment as a) but simulating a total failure coupling at position #10 and #20, respectively, by supplying the column with dry acetonitrile instead of the expected phosphoamidite building block solution in the respective coupling step (oligonucleotide nos. O3 and O4, repectively). The data obtained are shown in Table 1.

TABLE 1

| Exp. No.(SEQ.ID.NO.) | Product observed (5'-->3')* | MW** |
|---|---|---|
| a) 01(SEQ.ID.NO.1) | TsCsCsCsGsCsCsTsGsTsGsAsCsAsTsGsCsAsTsT | 6347.9/(6348.2) |
| b) 03(SEQ.ID.NO.3) | Octyl-sAsCsAsTsGsCsAsTsT | 3050.3/(3033.0) |
| c) 04(SEQ.ID.NO.4) | Octyl-sCsCsCsGsCsCsTsGsTsGsAsCsAsTsGsCsAsTsT | 6241.1/(6236.2) |

*: "s" = phosphorothioate residue/internucleosidic linkage
**: observed/(expected)

Capillary gel electrophoresis (CGE) analysis of the crude material of O1 reveales that the use of the lipocap capping procedure instead of the standard protocol does not disturbe the chain elongation. Furthermore, the use of the phosphoramidite compound (1) (see above) as capping reagent results in the complete blocking of chain elongation after pos. #10 and #20 in exp. b) and c), respectively. The compounds O1, O3 and 04 are identified by MALDI-TOF MS (U. Pieles et al., Nucleic Acids Res. 21 (1993), 3191). To estimate quantitatively the capping completion in experiment b) and c), aliquots are taken directly after the failure coupling and, in experiment b) at the end of the synthesis before the last detritylation. A partial capping would have resulted in the presence of trityl-on species in the crude material obtained from the second aliquot. Analysis by RP-HPLC reveales the absence of trityl-on species. Crude materials as present in both aliquots in experiment b) look identical and are characterized as the 9-mer O3. For experiment c) crude material is characterized as the 19-mer O4.

9. RP-HPLC Separation of a Full-length Oligonucleotide From a Corresponding Shortened Oligonucleotide Bearing the Lipocap Capping Group:

In order to check the usefulness of the lipophilic capping reagent (1) (see above) as an aid in the oligonucleotide purification on a hydrophobic stationary phase, the 19-mer oligonucleotide O4 (bearing the lipophilic cap, see above) is co-injected with the full length 20-mer O1 (see above). Analysis on RP-HPLC reveales a base-line resolution between the 20-mer (full-length material) and the 19-mer bearing the lipophilic capping group.

What is claimed is:

1. A process for the preparation of an oligomeric compound, comprising the step of: introducing a lipophilic capping group to an unreacted reactive group suitable for chain elongation of a not elongated oligomeric compound intended to be elongated in a preceding chain-elongation step, by reacting a lipophilic capping compound with the unreacted reactive group, wherein the lipophilic capping group is not removable during synthesis and work-up of the oligomeric compound; and wherein the not elongated oligomeric compound capped with said lipophilic capping group can be separated from the oligomeric compound on a hydrophobic stationary phase.

2. The process according to claim 1 wherein said oligomeric compound is selected from the group consisting of an oligonucleotide, an oligosaccharide and a glycopeptide.

3. The process according to claim 2, wherein said oligomeric compound is an oligonucleotide.

4. The process according to claim 1, wherein said unreacted reactive group is a hydroxy group.

5. The process according to claim 4, wherein said lipophilic capping compound is a compound selected from the group consisting of formula (I), (II), (III) and (IV)

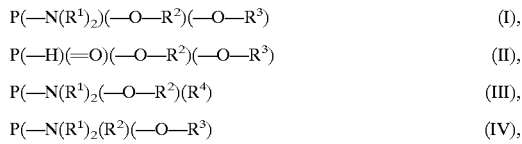

wherein
$R^1$ is alkyl, or $R^1$ together with the adjacent nitrogen atom forms a N-morpholino or N-pyrrolidino ring;
$R^2$ is a lipophilic substituent,
$R^3$ is a base-labile protecting group or a lipophilic substituent,
$R^4$ is a lipophilic substituent,
and wherein the lipophilic substituent forms a linkage to the adjacent respective oxygen or phosphorus atom which is stable during the synthesis and work-up of the oligomeric compound.

6. The process according to claim 5, wherein the lipophilic substituent is not bound via a fully substituted C-atom of an alkyl group to the respective adjacent oxygen atom or phosphorus atom.

7. The process according to claim 5 wherein said lipophilic substituent is of formula (V)

and wherein
m is an integer from 1 to 35;
n is 0 or 1;
$R^1$ and $R^6$ independently are H, branched or unbranched alkyl, unsubstituted or ring substituted aryl, or unsubstituted or ring substituted aralkyl, and wherein the substituent of said substituted aryl or aralkyl is selected from the group consisting of branched or unbranched alkyl, aryl or aralkyl;
X is O, S or $NR^8$;
$R^7$ is H or branched or unbranched alkyl; and
$R^8$ is branched or unbranched alkyl, aralkyl or aryl;
wherein aryl or aryl of aralkyl is an aromatic ring composed of at least 6 C-atoms;
provided that the substituent of formula (V) comprises at least one aryl or aralkyl substituent, or formula (V) comprises at least one linear alkyl backbone composed of at least 4 C-atoms.

8. The process according to claim 7, wherein $R^5$ and $R^6$ each are H, and $R^7$ is methyl, n is 0, and m is an integer from 3 to 35.

9. The process according to claim 8, wherein m is an integer from 4 to 18.

10. The process according to claim 9, wherein m is 7.

11. The process according to claim 5, wherein said lipophilic compound is a compound of formula (I)

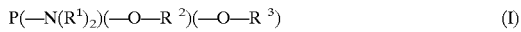
$$P(-N(R^1)_2)(-O-R^2)(-O-R^3) \qquad (I)$$

wherein $R^1$ is isoprfpyl, $R^2$ is $C_2)_7-CH_3$ and $R^3$ is β-cocyanoethyl.

12. The process according to claim 4 wherein said lipophilic compound is a compound of formula (I)

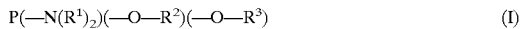
$$P(-N(R^1)_2)(-O-R^2)(-O-R^3) \qquad (I)$$

wherein $R^1$ is isopropyl, $R^2$ is $-(CH_2)_7-CH_3$ and $R^3$ is β-cyanoethyl.

13. The process according to claim 1, further comprising, after completion of the chain elongation of the oligomeric compound, the step of fully deprotectng the oligomeric compound, where a protected oligomeric compound is present.

14. The process according to claim 13, further comprising the step of separating the fully deprotected oligomeric compound from the capped not elongated oligomeric compound on a hydrophobic stationary phase.

15. A process for purification of an oligomeric compound, comprising the step of: separating a not elongated oligomeric compound capped with a lipophilic capping group from the oligomeric compound wherein the capped, not elongated oligomeric compound is obtainable by reacting a lipophilic capping compound with an unreacted reactive group of a not elongated oligomeric compound intended to be elongated in a preceding chain-elongation step, and wherein the lipophilic capping group is not removable during synthesis and work-up of the oligomeric compound, on a hydrophobic stationary phase.

16. The process according to claim 15, further comprising before the step of separation the step of fully deprotecting the oligomeric compound, where a protected oligomeric compound is present.

17. Use of a lipophilic compound as reagent for introduction of a lipophilic capping group to an unreacted reactive group, suitable for chain elongation of a not elongated oligomeric compound intended to be elongated in a preceding chain-elongation step of the synthesis of an oligomeric compound, wherein the lipophilic capping group is not removable during the synthesis and work-up of the oligomeric compound; and wherein the not elongated oligomeric compound capped with said lipophilic capping group can be separated from said oligomeric compound on a hydrophobic stationary phase.

* * * * *